United States Patent [19]

Lashmore et al.

[11] Patent Number: 5,318,746
[45] Date of Patent: Jun. 7, 1994

[54] PROCESS FOR FORMING ALLOYS IN SITU IN ABSENCE OF LIQUID-PHASE SINTERING

[75] Inventors: David S. Lashmore, Frederick; John A. Tesk, Highland, both of Md.; Moshe P. Dariel, Omer, Israel; Edward Escalante, Clarksburg, Md.

[73] Assignee: The United States of America as represented by the Secretary of Commerce, Washington, D.C.

[21] Appl. No.: 802,420

[22] Filed: Dec. 4, 1991

[51] Int. Cl.$^5$ .......................... B22F 1/02; A61C 5/10
[52] U.S. Cl. ......................................... 419/64; 419/2; 419/8; 419/35; 419/47; 427/570; 75/955; 433/223; 433/229; 264/19; 205/80
[58] Field of Search ................... 419/6, 35, 38, 39, 48, 419/49; 427/570; 205/80; 75/955; 264/19; 423/223, 229

[56] References Cited

U.S. PATENT DOCUMENTS

| | | | |
|---|---|---|---|
| Re. 29,093 | 12/1976 | Burns | 264/111 |
| 3,004,332 | 10/1961 | Werner | 29/182.5 |
| 3,914,507 | 10/1975 | Fustukian | 428/404 |
| 3,933,961 | 1/1976 | Burns | 264/111 |
| 4,181,757 | 1/1980 | Youdelis | 427/229 |
| 4,218,507 | 8/1980 | Deffeyes et al. | 428/328 |
| 4,323,395 | 4/1982 | Li | 75/212 |
| 4,426,404 | 1/1984 | Shoher et al. | 427/2 |
| 4,664,855 | 5/1987 | Tremblay et al. | 264/111 |
| 4,742,861 | 5/1988 | Shoher et al. | 164/80 |
| 4,859,412 | 8/1989 | Groll et al. | 419/23 |
| 4,963,184 | 10/1990 | Diehl et al. | 75/247 |
| 4,970,050 | 11/1990 | Groll et al. | 419/36 |
| 4,990,394 | 2/1991 | Shoher et al. | 428/212 |
| 4,997,699 | 3/1991 | Shoher et al. | 428/212 |
| 5,064,690 | 11/1991 | Sando et al. | 427/215 |
| 5,118,317 | 6/1992 | Wijner | 445/50 |
| 5,183,631 | 2/1993 | Kugimiya et al. | 419/10 |

OTHER PUBLICATIONS

Goetzel, C. G., "Treatise on Powder Metallurgy", pp. 248-250, 1949, vol. 1, Technology of Metal Powder and Their Products.
Greener et al., "Dental Amalgams", *Dental Materials: Properties and Selection*, Quintessence Publishing Co., Inc., 1989, pp. 263-281.
Masuhara et al., "Study on Toxicity of a New Gallium Alloy for Dental Restorations", *Journal of Dental Health*, 27, p. 361, (1987).
T. Okabe, "Characterization of a Gallium Alloy for Dental Restoration", *Dental Material Abstract* No. 624.
Ishii et al., "The Primary Irritant Testing to the Human Skin of Gallium Alloy", *J. Fukuoka Dent. Coll.*, 14(1):96-112, 1987, p. 49.
H. Joujima et al., "Studies on Biological Evaluation of Gallium Alloy", *J. Fukuoka Dent. Coll.*, 14(3):249-257, 1987, p. 40.
Yoshida et al., "The Basic Study on Gallium Alloy for Restoration", *J. Fukuoka Dent Coll.*, 31(4):1004-1012, 1988, pp. 1004-1005.
Kim et al., "The Clinal Observation of Gallium Alloy as a New Dental Restorative Material for Primary Teeth", *J. Fukuoka Dent. Coll.*, 14(4):395-400, 1988, p. 56.

*Primary Examiner*—Daniel D. Wasil
*Assistant Examiner*—Daniel Jenkins
*Attorney, Agent, or Firm*—Fran Wasserman

[57] ABSTRACT

Oxide-free metallic, alloy or intermetallic compound formed by coating a powder of at least one member selected from the group consisting of elemental metallic, alloy and intermetallic compound with an oxide-replacing metal. The oxide-free compound may be compacted without the addition of a liquid sintering agent and at temperatures below the melting point of the compound, under sufficient pressure to form a uniform, consolidated intermetallic body.

16 Claims, 7 Drawing Sheets

PROCESS FOR FORMING ALLOYS IN SITU IN ABSENCE OF LIQUID-PHASE SINTERING

FIELD OF THE INVENTION

The invention relates to a process of forming intermetallic alloys. In a preferred embodiment, the invention relates to processes for forming the intermetallic alloys as in situ dental restorations.

BACKGROUNDS

Amalgams and related alloys have been incorporated into a variety of commercial applications and thus a number of processes for producing such amalgams are known. For example, U.S. Pat. No. 4,664,855 discloses a universally employed process which triturates elemental metallics or an intermetallic alloy, in the form of comminuted filings or atomized spherical powders, with the sintering agent mercury and compacts the resulting amalgam into a uniform, consolidated intermetallic alloy. The process may be considered a combination of liquid phase and reactive metal sintering. The finely comminuted metallic or intermetallic powders react with the Hg and when pressure is applied to the reaction product, form a compact, high density mass. U.S. Pat. No. 3,933,961 discloses a process for preparing a pre-weighed alloy tablet of uniform weight which is then triturated with a weighed quantity of Hg to form a traditional amalgam alloy.

Metallic powders have two basic forms: 1) minute lathe-cut filings and 2) atomized, spherical particles. Lathe-cut filings are subsequently milled and sifted to produce the desired particle size. The length of particles in a commercial lathe-cut alloy might range from 60–120 $\mu$m long, 10–70$\mu$m wide and from 10–35$\mu$m thick. On the other hand, spherical particles, produced by means of an atomizing process whereby a spray of tiny drops is allowed to solidify in an inert gaseous (e.g., argon) or liquid (e.g., water) environment, have a maximum size between 40 and 50 $\mu$m (Dental Amalgams, William J. O'Brien, Ph.D., Quintessence Publishing Co., 1989, at p. 264, 266).

For more than 150 years, dental practitioners have applied a Ag-Sn system and related intermetallic alloys as dental amalgam preparations for use in dental restorations such as fillings and prostheses. The amalgamation reaction which forms Ag-Sn dental preparations is best represented below (Dental Materials, supra, at p. 269);

$$Ag_3Sn + Hg \rightarrow Ag_2Hg_3 + Sn_7Hg + Ag_3Sn;$$

or gamma + Hg → gamma 1 + gamma 2 + gamma (residual).

After completion of the amalgamation reaction, the high-melting Ag$_3$Sn (gamma) products are embedded in a matrix of mercury reaction products. Both the Ag$_2$Hg$_3$ (gamma 1) and Sn$_7$Hg (gamma 2) phases form a continuous network. In the amalgam structure above, however, the Sn$_7$Hg is susceptible to corrosion by the following reaction:

$$Sn_7Hg + 10\tfrac{1}{2}O_2 + 21H_2O + 14Cl^- \rightarrow 7Sn_4(OH)_6Cl_2 + 4Hg.$$

Dental amalgam corrosion results in a weakened structure and further formation of unsupported, "margin" amalgam which easily fractures under tension.

The introduction of contemporary amalgams in the 1960s (amalgams known as "high-copper" amalgams) eliminated the corrosive phenomenon of Sn$_7$Hg by preventing the formation of Sn$_7$Hg (gamma 2). However, even though the addition of Cu into amalgam alloys markedly improved the integrity of the dental amalgam, the Cu$_6$Sn$_5$ (the eta prime phase of the copper amalgam system) is prone to corrosion according to the following reaction (Dental Materials, supra, at 293).

$$2Cu_6Sn_5 + 4\tfrac{1}{2}O_2 + 9H_2O + 6Cl^{3-} \rightarrow CuCl_2 \cdot 3Cu(OH)_2 + {}^{10}SnO.$$

Furthermore, the copper which is known to leach out during corrosion of the high-copper amalgam systems has raised concern regarding the biocompatibility of these contemporary copper amalgams.

A more recent attempt to eliminate the well-known corrosive tendencies of the Ag-Sn and Ag-Sn-Cu amalgam systems is addressed in U.S. Pat. No. 4,181,757 which discloses a process for surface coating parent metals with a slurry (composed of a low-melting-temperature gold alloy powder, an inorganic oxide-dissolving flux, and organic liquid) and firing the slurry to produce a bonded, corrosion-resistant layer on the parent metal surface. The disclosed process is intended for use with dental prostheses and is not readily adaptable for in situ dental restorations such as fillings.

Additionally, recent evidence has raised new issues concerning the biocompatibility of currently used dental amalgams. Evidence has now been put forward that air expired by dental patients having dental restorations made from these amalgams, particularly after gum chewing, has a significantly higher mercury vapor content than that of amalgam free patients.

In an attempt to replace traditional dental amalgams with a more biocompatible intermetallic, experiments have been conducted on gallium alloys formed by triturating liquid gallium with a metal powder (Journal of Fukuoka Dental College, "Gallium Alloys for Dental Restorations,"Takashi Horibe et al., 12(4): 198–204, 1986). However, the Journal of Dental Health has reported that gallium alloys supplied orally to rats and mice induce toxic responses in the test subjects (J. of Dental Health, "Study on Toxicity of a New Gallium Alloy for Dental Restorations," 37. 361–371, 1987). This raises questions about their safety as an alternative to traditional amalgams used in dental restorations.

SUMMARY OF THE INVENTION

The invention pertains to an oxide-free metallic, alloy or intermetallic compound formed by coating a powder of at least one of either an elemental metallic, alloy or intermetallic compound with an oxide-replacing metal. The invention further pertains to a process for preparing an intermetallic alloy body by compacting the coated powder or a mixture of an elemental metallic powder and the coated powder without adding a liquid sintering agent to form an alloy body in situ. The compaction can be performed at temperatures below the melting points of the coated powder and a second elemental metallic powder and under sufficient pressure, to form a uniform alloy.

Intermetallic compounds and alloys produced in accordance with the present invention are substantially more biocompatible than existing commercial or experimental alloys.

DETAILED DESCRIPTION OF PREFERRED EMBODIMENTS

Figure 1:
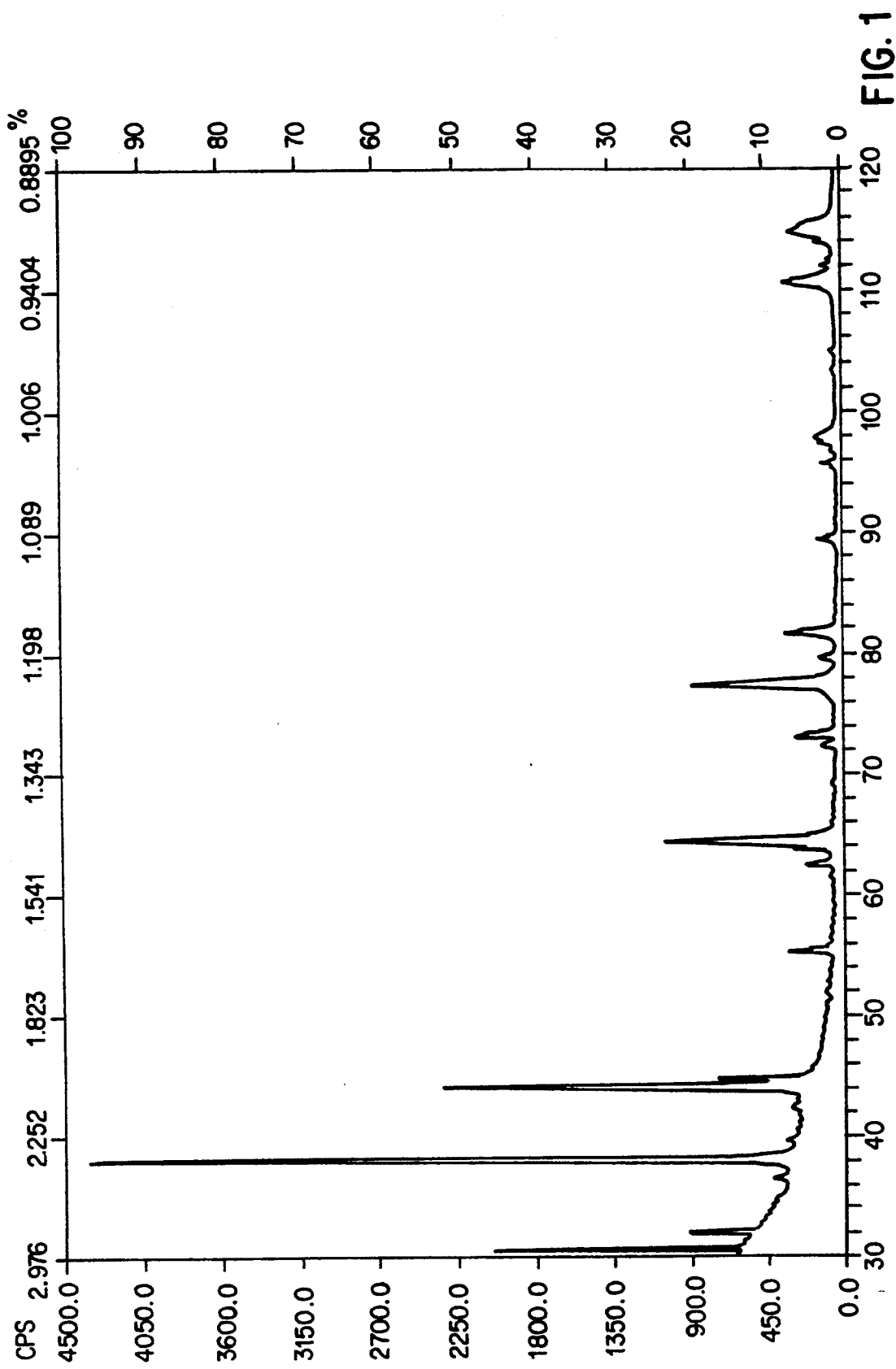
FIG. 1 is an x-ray diffraction spectrum for a compacted Ag-Sn intermetallic AGSN7.

A process for forming intermetallics according to the present invention which circumvents the need for liquid sintering agents such as mercury, relies on an alternative to the amalgamation process.

Such a "non-amalgamation" process involves the principle of fast-diffusion of metallic alloy or intermetallic powders. Fast-diffusion is attributed to the ability of the diffusing species to penetrate interstitially into the host matrix. Diffusion takes place via an interstitial mechanism instead of the usual vacancy mechanisms characteristic of diffusion in most metal systems. Interstitial diffusion is usually much faster than diffusion governed by the metal-vacancy mechanism.

In order to allow diffusion processes for metallic powders to reach completion in a reasonable time and at room temperature, naturally forming surface oxides are removed from the metallic, alloy or intermetallic powders. These surface oxides exist on most fast-diffusing metals and act as diffusion inhibitors.

When the naturally forming surface oxides of metal, alloy or intermetallic powders are removed completely, the metals, alloys or intermetallic compounds will form the desired intermetallic or related compounds without the use of a liquid sintering agent and under desirable conditions (for example, at or near body temperature and at pressures produced using normal or modified dental instruments in dental applications).

Therefore, the present invention involves producing at least one of an oxide-free metallic alloy or intermetallic compound by replacing the surface oxides with a non-oxidizing metal or a metal that forms a nontenacious oxide.

In an electrochemical process, an elemental metallic, alloy or intermetallic powder is coated with an oxide-replacing metal, such as Ag, Au, Pd or Pt, by immersing the powder in a solution containing an electrolyte, and subsequently separating, by vacuum filtration, evaporation or other suitable means, the coated powder from the electrolyte solution.

Examples of electrolytes useful in the present application include, but are not limited to, Ag, Au, Pd and Pt salts of the cyanide, nitrate, pyrophosphate and sulfide ions. The silver salt of the nitrate ion is preferred and is preferably used in concentrations ranging from about $1 \times 10^{-5}$ to about $1 \times 10^{-2}$M and more preferably in a concentration of about $1 \times 10^{-2}$M.

Other methods for removing oxides and preventing further oxide formation, than the electrochemical method described above, may also be used. For example, gas plasmas with inert or reducing atmospheres, such as a forming gas (5% $H_2$ and 95% $N_2$), also remove surface oxides from metals. Similarly, vapor deposition or sputtering will coat the powder with protective layers of Ag, Au or a related alloy.

Metal dendrites which form during electrolytic oxide removal inhibit the diffusion of the powders upon compaction. A metal complexing agent added to the electrolyte solution reduces the formation of undesirable metal dendrites on the powder surfaces. Examples of metal complexing agents suitable for use in the present invention include, but are not limited to, ammonia, citrate, ethylenediaminetetraacetic acid, pyrophosphate, sodium chloride, tetrasodium pyrophospate, sodium potassium tartrate, sulfamate, sulfite and thiourea. Thiourea is a preferred metal complexing agent. It is preferably used in concentrations of from about $1 \times 10^{-5}$ to $1 \times 10^{-3}$M, and more preferably in concentrations of about $1 \times 10^{-3}$M.

Addition of other metal dendrite suppressing agents to the electrolyte solution will also suppress undesirable dendrite growth. Examples of metal dendrite suppressing agents suitable for use in the present invention include, but are not limited to, salts of Au, Pt, Pd or Ir, as for example, $AuCl_2$, $PtCl_2$ and $PdCl_2$. $AuCl_2$ is a preferred metal dendrite suppressing agent. It is preferably used in concentrations of about $1 \times 10^{-5}$M to about $1 \times 10^{-3}$M.

Examples of metallic powders coated in accordance with the present invention include, but are not limited to, powders of Au, Ag, Co, Cu, Fe, Ga, In, Ir, La, Ni, Pd, Pt, Re, Rh, Ru, Sn, Ti, Y or Zn. Sn is preferred.

Typically, when compacted at clinical temperatures and under pressures achieved using dental instruments, many metals have such low fast-diffusion reaction rates at body temperatures that their use in dental applications is impractical.

The biocompatible Ag-Sn system in accordance with the present invention belongs to a group of binary metallic systems that have been found to exhibit so-called "ultra-fast diffusion" behavior. These members include Ag, Au, Co, Cu, Ga, In and Sn. Ultra-fast diffusion is characterized by diffusion rates higher, by many orders of magnitude, of a small size, low-valence constituent (e.g., Ag) within the matrix of the large size, usually high valence component (e.g., Sn). Similar behavior has been observed for mono-valent metals (e.g., Ag, Au and Cu) and some transition metals (e.g., Co, Fe, Ni and Pd) as diffusing species and Zn, Group IV-B metals (e.g, Sn) and transition metals (e.g., La, Ti, Y and Zn) as active metal matrices.

Examples of alloys or intermetallic powders useful in the present invention include but are not limited to powders having at least one first elemental metal selected from the group consisting of La, Sn, Ti, Y and Zn and at least one second elemental metal selected from the group consisting of Ag, Au, Co, Cu, Fe, In, Ir, Ga, Ni, Pd, Pt, Re, Rh and Ru.

A preferred alloy or intermetallic powder contains a first elemental metal, Sn, and a second elemental metal, Ag. A preferred Ag:Sn atomic ratio of the Ag-Sn alloy or intermetallic powder is from about 1:1 to about 10:1. More preferably, the Ag:Sn atomic ratio is about 3:1. Properties of the Ag-Sn intermetallic compound can be altered by blending small additions of elemental powders with other powders or by small additions of elements to the alloy or intermetallic powders.

After the elemental metallic, alloy or intermetallic powder is coated with an oxide-replacing metal, a consolidated alloy body such as dental restoration may be formed, in situ (e.g., in a dental cavity or mold for a commercial mounting press), by compacting at least one of the oxide-free, coated powders or a mixture of an elemental metallic powder and a coated powder, preferably without adding a liquid sintering agent. Examples of compacting include, but are not limited to, "hipping" (hot isostatic pressing) and "hot pressing."

An in situ dental restoration, as for example dental fillings, is a preferred application of the compacted alloy thus formed. In one embodiment of the invention, Ag and Sn powders, separately coated with an oxide-replacing metal, are compacted at body temperature.

A preferred coated powder used in dental applications is Sn and a preferred elemental powder is Ag with a preferred Ag:Sn atomic ratio of the Ag-Sn alloy or intermetallic powder ranging from about 1:1 to about 10.1. Preferably, the intermetallic powder is $Ag_3Sn$ with Sn being present in a near stoichiometric excess.

The in situ formation of the alloy preferably occurs at a temperature below the melting point of the coated powders and under an applied pressure. Exemplary ranges of temperature and pressure under which the alloys may be formed include, but are not limited to, from about 20° C. to about 100° C., and from about 20 KSI (1KSI=1000PSI) to about 75 KSI, respectively. A preferred temperature for alloy formation is about body temperature. A preferred pressure is about 45 KSI.

It is preferred to keep the diffusion lengths of the metallic or intermetallic components down to the order of 2 to 5 $\mu$m. Therefore, in the process for preparing intermetallic alloys according to the present invention, powders have an exemplary equiaxial particle size of from about 0.5 $\mu$m to about 100 $\mu$m. Preferably, the particle size of the powders will range from about 0.5 $\mu$m to about 50$\mu$m.

Ag-Sn intermetallic powders having atomized, spherical particles with particle sizes ranging from 2 $\mu$m to 50 $\mu$m are preferred in the electrochemical process for producing an oxide-free metallic or intermetallic compound. The preferred $Ag_3Sn$ intermetallic powder compacted to form the in situ alloy is preferably comprised of atomized, spherical particles having a particle size of from 0.5 $\mu$m to 50 $\mu$m.

Exemplary preparation and properties of powders and alloys formed according to the present invention will be described in the following examples.

EXAMPLES

Example 1

A $1.0\times10^{-2}$M $AgNO_3$ electrolyte solution and $1\times10^{-4}$M thiourea solution are prepared according to the following procedure:

1.90365 grams of thiourea are weighed and added to 250ml of distilled water to make a $1.0\times10^{-1}$M thiourea solution. 25ml of the $1.0\times10^{-1}$M thiourea solution are pipetted and added to 250 ml of distilled water to make a $1.0\times10^{-2}$M thiourea solution. A final 25 ml volume of the $1\times10^{-2}$M thiourea solution is pipetted and added to 250 ml of distilled water to make $1.0\times10^{-3}$M thiourea solution.

16.992 grams of silver nitrate are measured and added to 1 liter of distilled water in a 1 liter flask to make a $1.0\times10^{-1}$M $AgNO_3$ solution. 25ml of the $1.0\times10^{-1}$M $AgNO_3$ are pipetted and mixed with a 25ml pipetted volume of the $1.0\times10^{-3}$M thiourea solution. The 50 ml $AgNO_3$ and thiourea solution is then diluted to 250ml with distilled water to make a $1.0\times10^{-2}$M $AgNO_3$, $1.0\times10^{-4}$M thiourea electrolyte solution.

A commercially available 2.5 g/l $AuCl_2$ ($1.3\times10^{-3}$M) solution is used as a metal dendrite suppressing agent.

2.4363 grams of Fisher Sn powder, Cat. No. T129, Lot No. 743145, are weighed and added to a Buchner filter. 25 cc of a 1:1 solution of the $1.0\times10^{-2}$M $AgNO_3$, $1.0\times10^{-3}$M thiourea and $1.3\times10^{-3}$M $AuCl_2$ solution is added to the Buchner filter and stirred for four minutes. The mixture containing the Sn powder is allowed to sit for one minute and the liquid is then removed by vacuum filtration. The resulting coated powder is rinsed twice with distilled water and dried for 48 hours.

Example 2

A $1.0\times10^{-2}$M $AgNO_3$ and $1.0\times10^{-3}$M thiourea solution is prepared as directed in Example 1. 4259 grams of Fisher Sn metal powder are weighed and placed in a Buchner filter. 20cc of the $1.0\times10^{-2}$M $AgNO_3$, $1.0\times10^{-3}$M thiourea solution is added to the Buchner filter containing the Sn metal and stirred with a glass rod for four minutes. The electrolyte solution containing the Sn powder is allowed to sit for one minute and then filtered for 30 minutes to remove the electrolyte solution using vacuum filtration. A sufficient quantity of distilled water is added to rinse the resulting coated powder and the distilled water is filtered off by vacuum filtration. A final rinse is performed using commercially available spectral grade methanol. The Buchner filter containing the coated Sn powder is then placed in a vacuum desiccator for one hour. The damp powder and Buchner filter are then removed from the vacuum desiccator and the powder is removed from the Buchner filter, placed on an evaporating dish and evacuated for approximately one hour.

Figure 2:
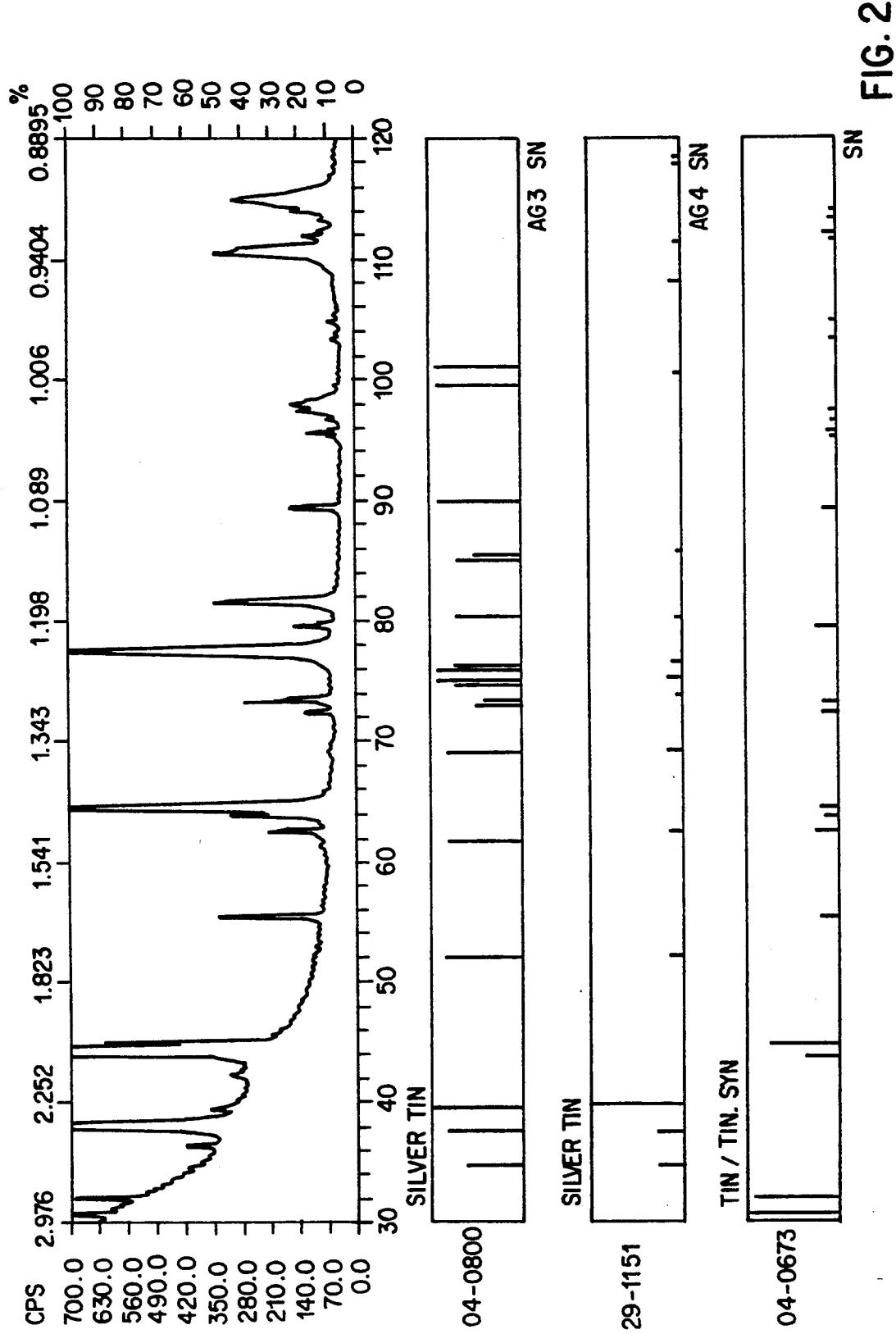
FIG. 2 is a second x-ray diffraction spectrum for the sample in FIG. 1.

The coated and dried Sn powder prepared above is mixed with 4.2778 grams of Fisher Ag powder. A commercially available dental mixer (Vortex-Genie mixer model S8223, Scientific Products) is used to blend the Sn and Ag powders in a 0.25 inch diameter mold for the PR-22 mounting press. The powder is then heated to 100° C. for approximately 1 hour and compacted at 22 KSI. The resulting consolidated Ag-Sn intermetallic is labeled as AGSN7 and an x-ray diffraction analysis is conducted. FIGS. 1 and 2 are the resulting x-ray diffraction spectra. Using a TUKON microhardness tester, the Knoop hardness of sample AGSN7 is determined and reported in Table I.

Example 3

A 1:1 solution of $1.0\times10^{-2}$M $AgNO_3$, $1.0\times10^{-3}$M thiourea and $1.3\times10^{-3}$M $AuCl_2$ is made by mixing 15 cc of the $1.0\times10^{-2}$M $AgNO_3$, $1.0\times10^{-3}$M thiourea solution (prepared according to the procedure in Example 1) to 15 cc of $1.3\times10^{-3}$M $AuCl_2$ solution. The resulting 1:1solution is then filtered through a fine Buchner filter. A non-excess of $AgNO_3$ is verified by combining a drop of the 1:1 solution and a drop of $AgNO_3$ which causes AgCl to precipitate. A 0.6945 gram sample of Sr: powder is weighed and mixed with 5 cc of the above prepared 1:1 electrolyte solution and stirred for four minutes. The electrolyte solution and powder are allowed to rest for one minute. 2.0853 grams of Ag powder are then added to the existing electrolyte solution in the medium Buchner filter and mixed for 30 seconds. A partial evacuation removes some liquid through the filter until the mixture remains "moist." The resulting powders are rinsed with 10 cc of distilled water and the water is removed by vacuum filtration. The mixture is then mixed with a spatula and some material is placed in a 0.25 inch diameter compression mold and compacted to 43.6 KSI at 36° C. for 10 hours.

Figure 3:
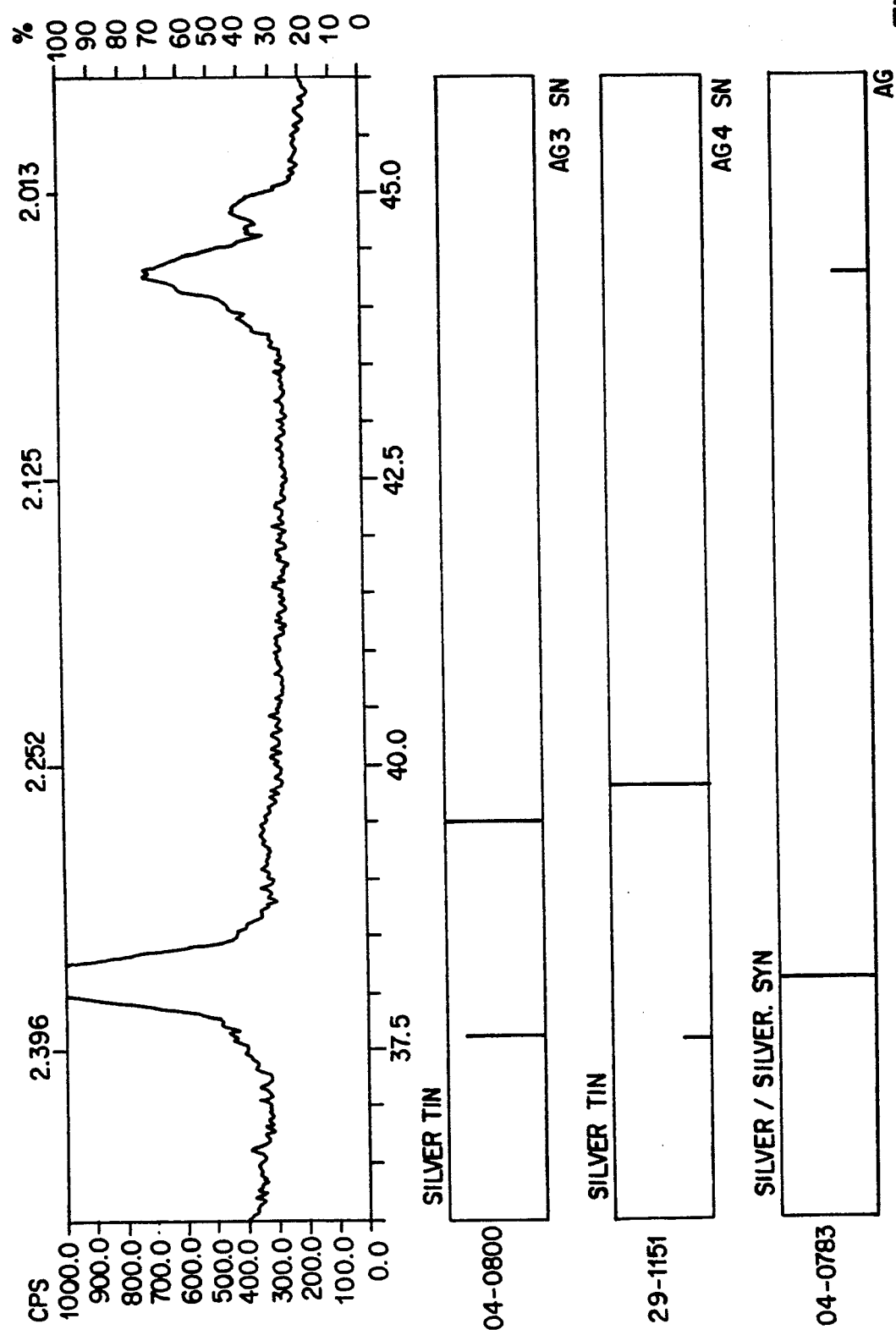
FIG. 3 is an x-ray diffraction spectrum for a compacted Ag-Sn intermetallic sample, AGSN19.

A portion of the remaining powder mixture is placed in a "Baker-test your adaptation" lucite mold and compacted and consolidated using dental tools for compacting and burnishing. The mold and consolidated intermetallic powder, which develops a shiny, metallic appearance, is annealed overnight at 40° C. The sample, AGSN19, is x-rayed and the resulting x-ray diffraction spectrum is shown in FIG. 3. The Knoop hardness of AGSN19 is shown in Table I.

Example 4

A 1:1 solution of $1.0 \times 10^{-2}$M $AgNO_3$, $1.0 \times 10^{-3}$M thiourea and $1.3 \times 10^{-3}$ M $AuCl_2$ is prepared by combining 25 cc of the $1 \times 10^{-2}$ M $AgNO_3$, $1 \times 10^{-3}$ M thiourea solution as prepared in Example 1 with 25 cc of $1.3 \times 10^{-3}$ M $AuCl_2$ solution as used in Example 2. The resulting 50 cc of solution are filtered through a fine Buchner filter.

Figure 4:
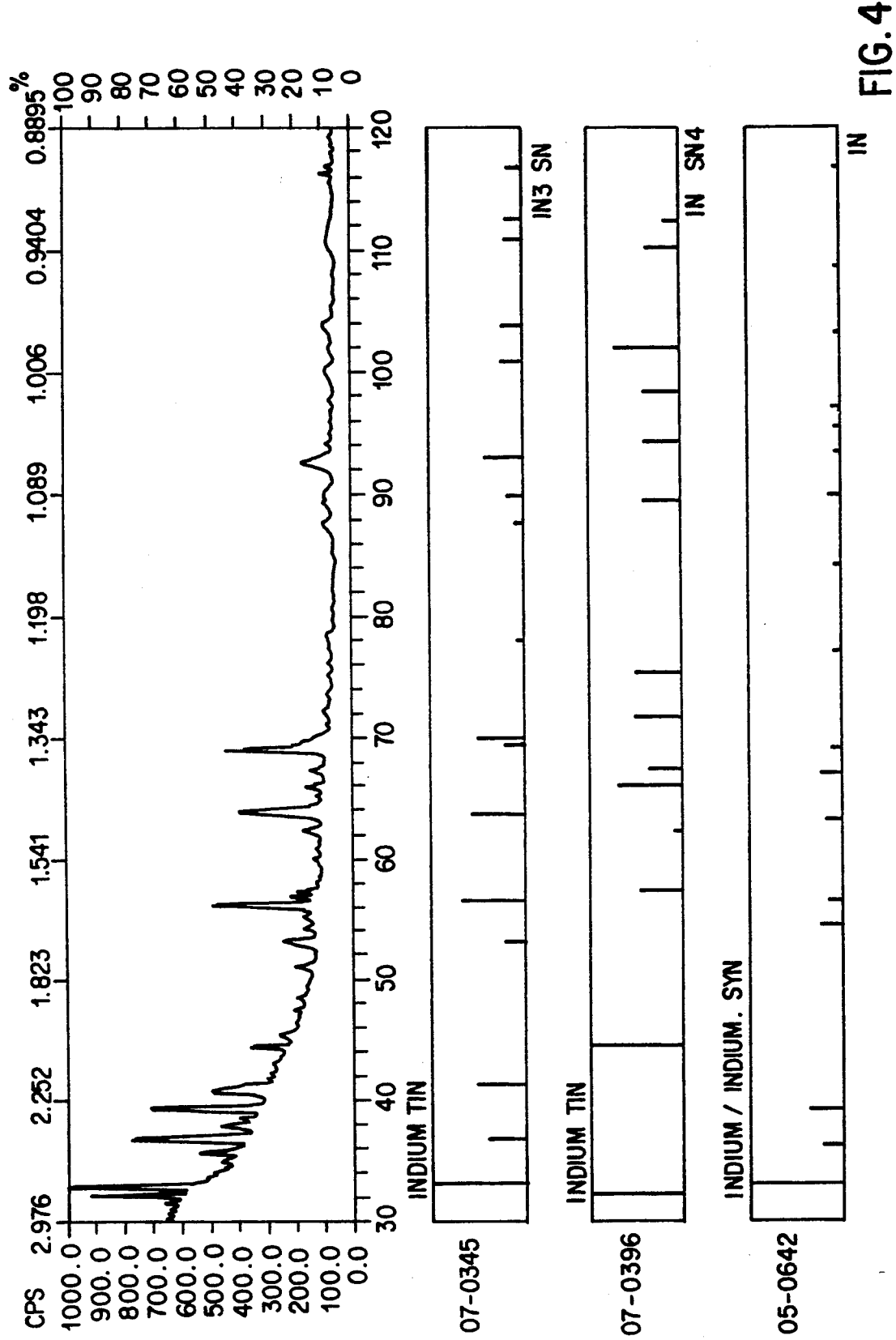
FIG. 4 is an x-ray diffraction spectrum for an In-Sn compacted sample, INSN1.
Figure 5B:
FIGS. 5a and 5b are electron micrographs of a compacted Ga-Sn sample, DL1.
Figure 5A:
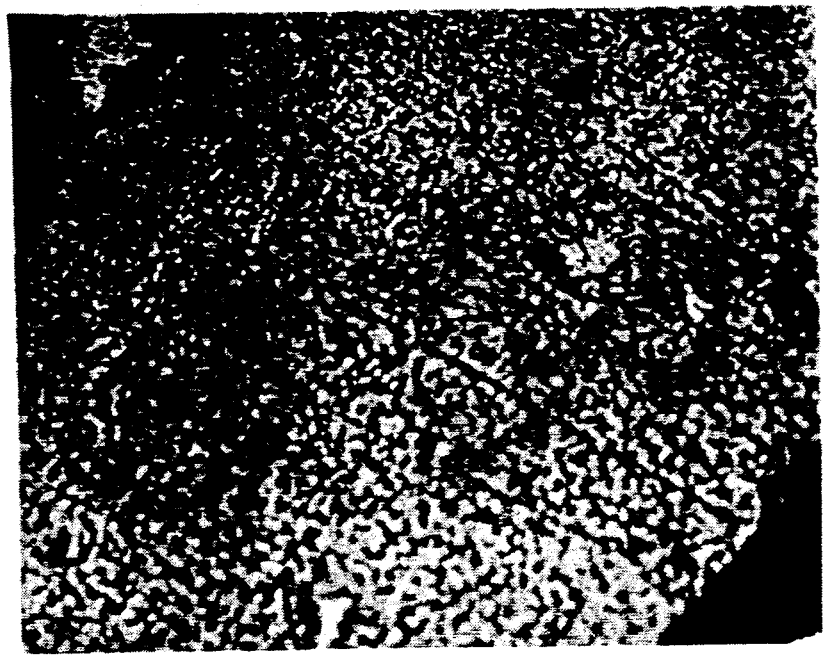
Figure 6B:
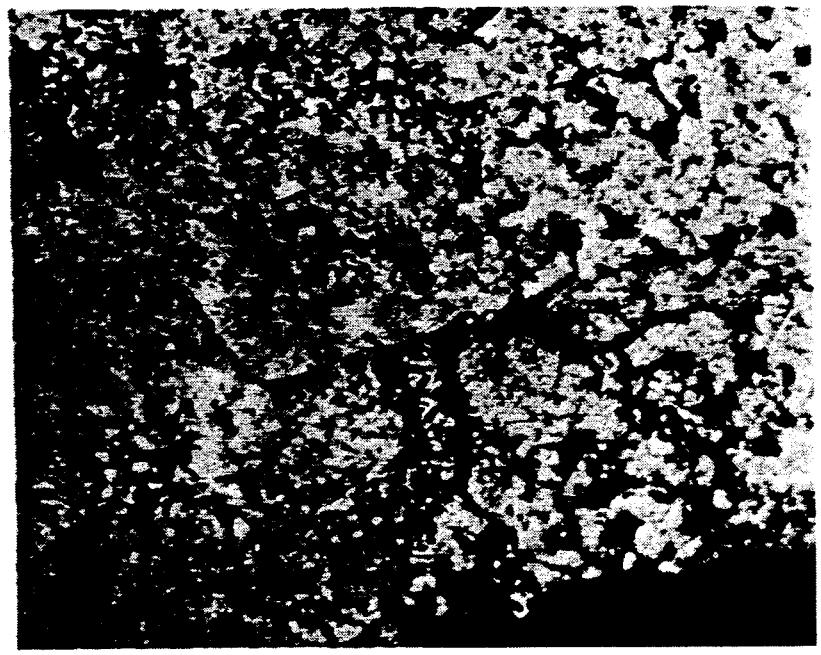
FIGS. 6a and 6b are electron micrographs of a compacted Ga-Sn sample, DL2.
Figure 6A:
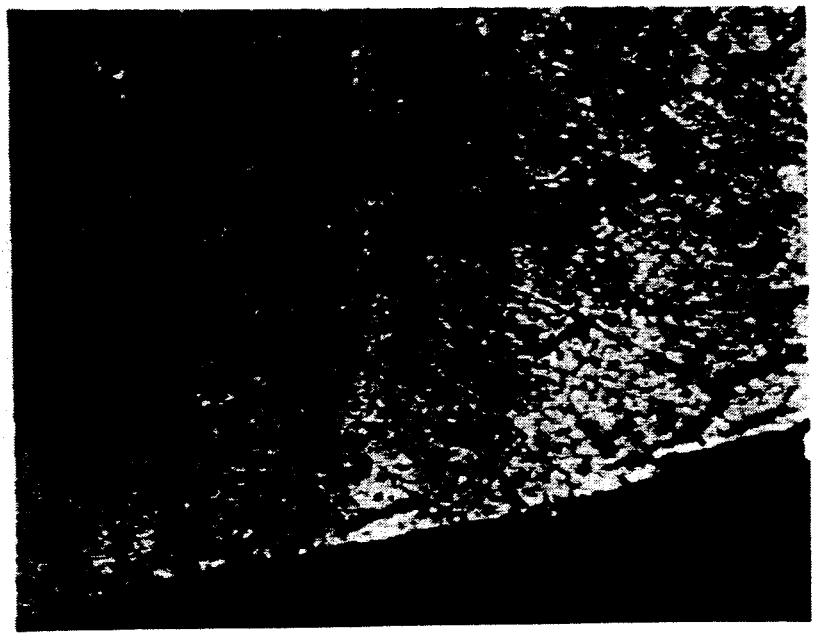
Figure 7B:
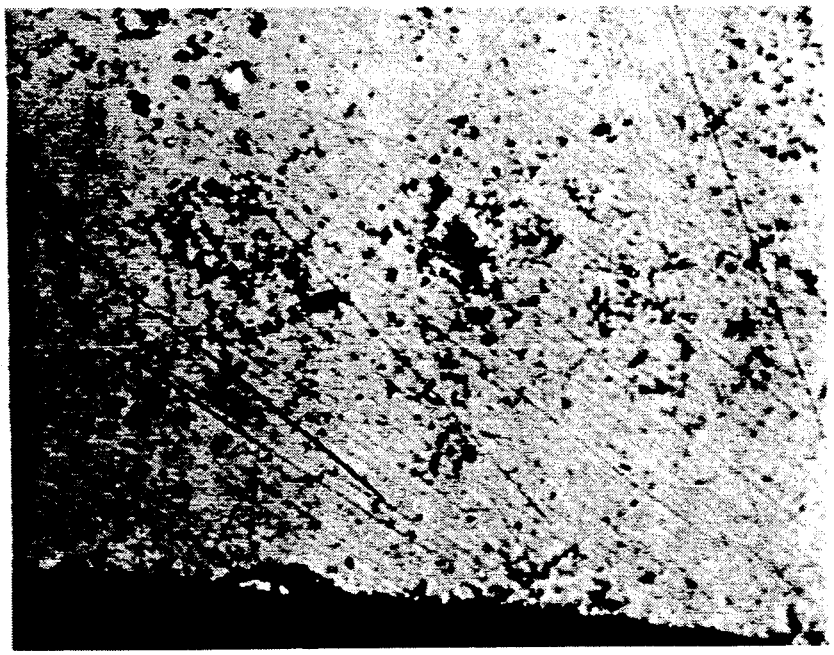
FIGS. 7a and 7b are electron micrographs of a compacted Ga-Sn sample, EE1.
Figure 7A:
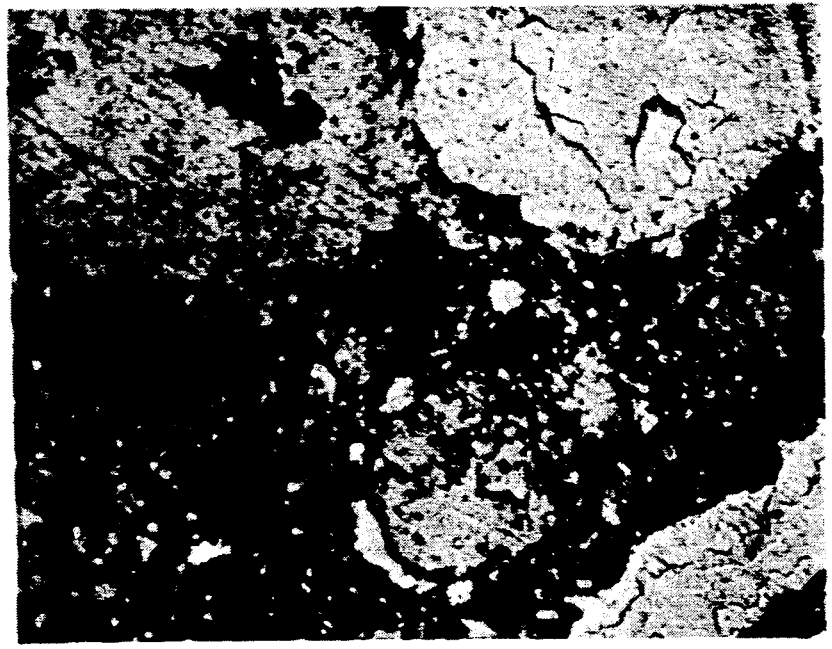

0.4772 grams of pure Sn powder prepared above are weighed and combined with a weighed 1.9090 gram sample of Indium powder. The two powders are weighed in plastic test tubes, and manually mixed. Indium powder is broken up manually. The manually mixed powders are then mixed using a dental "shaker" (such as a "Wig-L-Bug Amalgammator," Model LP-60, from Crescent Dental Mfg. Co.) for 30 seconds. A 1.0 gram weighed sample of the Sn-In intermetallic powder is placed in a 0.25 inch diameter mold and compressed to 21 1 KSI at room temperature for 10 minutes. After 4 minutes, the pressure drops, but continuous and subsequent pumping returns the pressure to 21KSI. Upon removal from the compression mold, the material is reacted, is liquified and forms a thin foil specimen within the mold. A small round sample is cut from the foil specimen, INSN1, and an x-ray diffraction pattern obtained. The resulting diffraction spectrum is shown in FIG. 4. The Knoop hardness results are shown in Table I.

Example 5

Small granular Ga material is prepared for use by smashing between the polished ends of two stainless steel cylinders (approximately 1.5 and 2cm in diameter). 0.3207 grams Sn powder are weighed in a plastic test tube and 0.9616 grams Ag powder are weighed and added to the plastic test tube. The resulting combined powder is mixed well with a Vortex-Genie dental mixer for approximately 30 seconds. A 0.06044 gram sample of the above crushed Ga is weighed out and a small particle of the crushed Ga (approximately 1 mm diameter) is placed in a "Baker" plastic mold. A small amount of the 3:1 Ag-Sn powder prepared above is added, mixed and then compressed with dental tools. One additional specimen is prepared in a like manner. A third compact intermetallic is layered until a small "pill" is formed. The specimens are labeled DL1, DL2 and EE1, respectively. Micrographs for the above specimens (DL1, DL2 and EE1) are shown in FIGS. 5a and 5b, 6a and 6b and 7a and 7b.

TABLE I

Calculated Hardness Values Using 50 g Load
(Except Where Indicated)
+++++++ Comminuted Alloys +++++++

| Specimen | Dial Units | Calculated Knoop Hardness ($K/mm^2$) | Average |
|---|---|---|---|
| AGSN7 | 503 | 61.6 | 53.6 |
|  | 584 | 45.7 |  |
| AGSN19 | 572 | 47.6 | 46.9 |
|  | 581 | 46.2 |  |
| INSN1 (5 g load) | 926 | 1.8 | 1.9 |
|  | 878 | 2.0 |  |

What is claimed is:

1. A process for preparing an intermetallic alloy body comprising the steps of:
   a) coating a first powder of at least one member selected from the group consisting of elemental metallic, alloy and intermetallic compounds with an oxide-replacing metal; and
   b) compacting the coated first powder or a mixture of an elemental metallic second powder and the coated first powder without adding a liquid sintering agent to form an alloy body in situ.

2. The process according to claim 1 wherein the compacting of the coated first powder and elemental second powder is done by hipping.

3. The process according to claim 1 wherein the compacting of the coated first powder and elemental second powder is done by hot pressing.

4. The process according to claim 1 wherein the coated first powder is coated Sn and the elemental second powder is Ga.

5. The process according to claim 4 wherein the Ga and Sn are used in an atomic ratio of about 1:20.

6. The process according to claim 1 wherein the coated first powder is a coated Ag-Sn intermetallic and the elemental second powder is Ga.

7. The process according to claim 1 wherein the compacting takes place at a temperature below the melting points of the coated first powder and the second powder and under an applied pressure.

8. The process according to claim 7 wherein the temperature is in a range of from about 20° C. to about 100° C. and the applied pressure is in a range of from about 20 KSI to about 75 KSI.

9. The process according to claim 7 wherein the applied pressure ranges from about 20 KSI to about 75 KSI.

10. A process for preparing an intermetallic dental restoration comprising the steps of:
    a) coating a first powder of at least one member selected from the group consisting of elemental metallic, alloy and intermetallic compounds with an oxide-replacing metal; and
    b) compacting orally, in situ, the coated first powder or a mixture of an elemental metallic second powder and the coated first powder without adding a liquid sintering agent to form the dental restoration.

11. A process for preparing an intermetallic alloy body comprising the steps of:
    a) coating a first powder of at least one member selected from the group consisting of elemental metallic, alloy and intermetallic compounds with an oxide-replacing metal; and b) compacting the coated first powder or a mixture of an elemental metallic second powder and the coated first powder at approximately body temperature and under an applied pressure without adding a liquid sintering agent to form an alloy body in situ.

12. A process for preparing an intermetallic alloy body comprising the steps of:
    a) coating a first Sn powder with an oxide-replacing metal; and
    b) compacting the coated first Sn powder or a mixture of an elemental metallic second Ag powder and the coated first Sn powder without adding a liquid sintering agent to form the alloy body in situ.

13. The process according to claim 12 wherein an atomic ratio of Ag in said second powder to Sn in said coated first powder ranges from about 1:1 to 10:1.

14. A process for preparing an intermetallic alloy body comprising the steps of:
    a) coating a first powder of $Ag_3Sn$ atomized, spherical particles having an equiaxial particle size of from about 0.5 $\mu$ to about 50 $\mu$ with an oxide-replacing metal; and
    b) compacting the coated first powder or a mixture of an elemental metallic second powder and the coated first powder without adding a liquid sintering agent to form an alloy body in situ.

15. The process according to claim 14 wherein the first powder before coating has an equiaxial particle size of from about 0.5 $\mu m$ to about 50 $\mu m$.

16. A process for compacting Ag and Sn powders at body temperature, in situ whereby the Ag and Sn powders are separately coated with an oxide-replacing metal.

* * * * *